Figure 1:
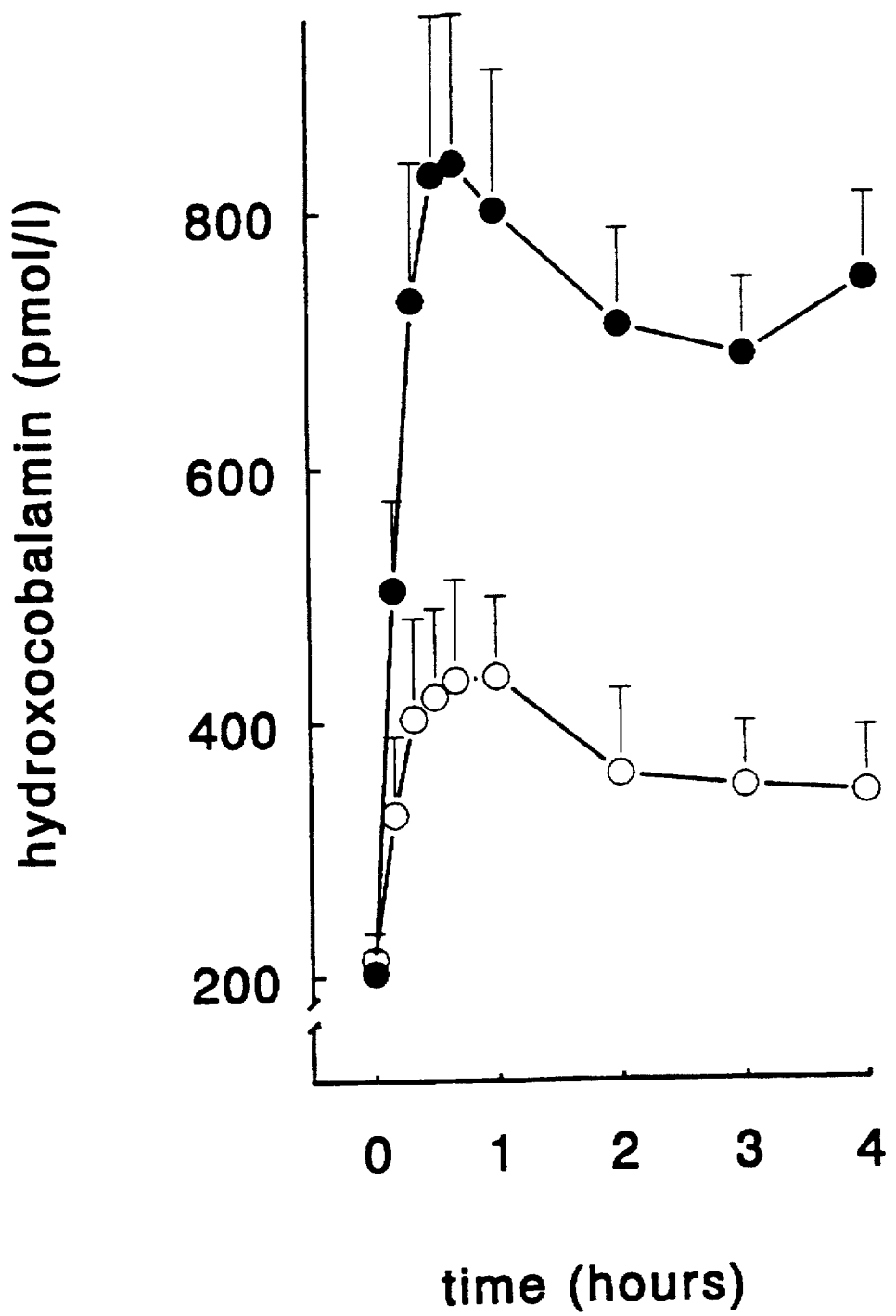

United States Patent [19]

Merkus

[11] Patent Number: 5,801,161
[45] Date of Patent: Sep. 1, 1998

[54] PHARMACEUTICAL COMPOSITION FOR THE INTRANASAL ADMINISTRATION OF HYDROXOCOBALAMIN

[76] Inventor: Franciscus W. H. M. Merkus, Groot Reesdijk 26, Kasterlee 2460, Belgium

[21] Appl. No.: 663,240
[22] PCT Filed: May 13, 1994
[86] PCT No.: PCT/EP94/01567
§ 371 Date: Jun. 17, 1996
§ 102(e) Date: Jun. 17, 1996
[87] PCT Pub. No.: WO95/17164
PCT Pub. Date: Jun. 29, 1995

[30] Foreign Application Priority Data

Dec. 20, 1993 [BE] Belgium .................. 9301418

[51] Int. Cl.⁶ .................................................. A61K 31/70
[52] U.S. Cl. .................................................. 514/52
[58] Field of Search .................................................. 514/52

[56] References Cited

U.S. PATENT DOCUMENTS 3,903,253  9/1975  Rolland .................. 514/52

FOREIGN PATENT DOCUMENTS

86/05987  10/1986  WIPO.
86/05988  10/1986  WIPO.

Primary Examiner—Raymond Henley, III
Attorney, Agent, or Firm—Jones, Day, Reavis & Pogue

[57] ABSTRACT

The invention relates to a pharmaceutical formulation, in a composition and form suitable for nasal administration, containing hydroxocobalamin dissolved in a concentration about 1% (w/w), having a viscosity of less than 1000 cP.

4 Claims, 1 Drawing Sheet

PHARMACEUTICAL COMPOSITION FOR THE INTRANASAL ADMINISTRATION OF HYDROXOCOBALAMIN

This application is a 371 of PCT/EP94/101567 filed May 13, 1994.

The invention is related to a pharmaceutical composition for the intranasal administration of hydroxocobalamin, a substance from the Vitamin B12 family.

Vitamin B12 has been first isolated in 1948 and since that time it is widely used in therapeutically active drugs in the treatment of pernicious anemia and other vitamin B12 deficiency disorders. These diseases are mainly caused by an inadequate absorption of Vitamin B12 from the gastrointestinal tract.

Vitamin B12 occurs in the human body as methylcobalamin, adenosylcobalamin, hydroxocobalamin and cyanocobalamin. Only cyanocobalamin and hydroxocobalamin are used in the treatment of patients.

Oral, sublingual as well as nasal administration of Vitamin B12 appeared to be ineffective treatments and therefore administration by intramuscular injection is the only satisfactory and medically accepted therapy up to now. However, intramuscular injections of Vitamin B12 have many disadvantages, especially because this drug is often administered to older people. Such people may have reduced muscle mass or are atrophic, so that repeated injections are inconvenient and painful, and also require doctor's visits. Maintenance therapy with Vitamin B12 means at least monthly injections and must be continued for life.

Already in 1953 Monto et al (Am. J. Med. Sci., 1953, Vol.225, pages 113–119) published a study related to an alternative route for administering Vitamin B12, i.e. nasal inhalation aiming at deposition of therapeutically active material in the lungs. Cyanocobalamin in lactose powder and in physiological saline solutions, containing 15 to 200 µg crystalline cyanocobalamin per ml, were used for nasal inhalation. The results of this investigation of Vitamin B12 administration by inhalation were reported as encouraging, but constituting only preliminary observations regarding the efficiency of inhalation crystalline cyanocobalamin treatment of pernicious anemia. The publication mentioned that intranasal B12 drops and dust, as routes of administration, were also under investigation by that time.

Israëls and Shubert (The Lancet, Feb. 13, 1954, pages 341–343) stressed the disadvantage of having no alternative for the intramuscular administration of Vitamin B12 and published some experiences supporting some of the findings of Monto et al (1953), i.e. Vitamin B12 seems to be therapeutically effective when administered by inhalation as a powder.

In 1954 Monto et al published further experiences, with nasal inhalation and installation of crystalline Vitamin B12 (Arch. of Int. Med. 93, 1954, pages 219–230). They reported a good hemopoietic effect after nasal administration of cyanocobalamin in lactose powder or in a dose of 100 µg per ml in a saline solution. Although the therapy was characterized as being not only effective but safe and economical, there was no follow up or any factual medical use of the therapy in the subsequent decennia. Since the urgent need for an alternative administration route continued to exist, apparently, the conclusions in the publications were too optimistic.

Other proposals for intranasal administration of Vitamin B12 are described in PCT/US 86/00665 and PCT/US 86/00793. Both proposals are based on the assumption that previous experiments failed, because of the fact that the administered cyanocobalamin, in a solution or powder, did not remain in the nasal cavity, but passes the nose to the throat or lungs. To solve this problem, both patent applications propose that the nasal formulation should stay for a much longer time in the nasal cavity. To obtain this longer residence time the formulation is administered in the form of an aerosol (PCT/US/86/00665) or the formulation should possess an enhanced viscosity, above 2500 cP (PCT/US/86/00793). This should give a consistent, continuous and uniform absorption of Vitamin B12. A concentration from 0.05% to 1% by weight based on the total weight is described as typical concentrations of Vitamin B12 in the compositions of both patent applications.

Extensive investigations have been carried out by applicant into the mechanism of the nasal absorption through the nasal epithelium of hydroxocobalamin and cyanocobalamin. For that purpose both substances were administered nasally in isotonic aqueous solutions to human volunteers. The investigations have lead to the new insight into the underlying mechanism of the nasal absorption of Vitamin B12.

For the nasal absorption of Vitamin B12, the longer nasal residence time of the formulation or the amount or volume of the formulation are of no or minor importance. The extent of the nasal absorption of Vitamin B12 is mainly and principally governed only by the concentration of Vitamin B12 in the nasal formulation.

A high and efficient intranasal absorption of Vitamin B12 is advantageous in medical therapy, and can be obtained only by using hydroxocobalamin, which shows a significant higher solubility in water than cyanocobalamin. Only with hydroxocobalamin a superior nasal composition in an aqueous medium can be produced with by far the highest concentration of Vitamin B12 and consequently a much more efficient nasal absorption of Vitamin B12. Such a nasal formulation can be taken less frequently by patients, making the therapy much easier and less expensive.

DESCRIPTION AND EXAMPLE

The following experiments were conducted in 6 healthy male volunteers to establish the bioavailability, which means the extent and rate of absorption, of a nasally administered Vitamin B12. For the study only non-smokers were selected, because in smokers serum levels of Vitamin B12 can be found, which deviate from normal levels. Serum levels were measured by radioimmunoassay and expressed in pMol/l.

The results of the first experiment are summarized in table 1.

TABLE 1

Vitamin B12 serum concentration in 6 volunteers after nasal administration of hydroxocobalamin in an isotonic aqueous solution.
dose: 500 µg hydroxocobalamin HCl
volume: 100 µl
concentration: 500 µg/100 µl = 50 µg/100 mg = 0.5%

| Time after administration (minutes) | Vit B12 pMol/l | Standard deviation (n = 6) |
|---|---|---|
| 0 | 214 | 21 |
| 10 | 328 | 61 |
| 20 | 403 | 79 |
| 30 | 420 | 69 |
| 40 | 433 | 71 |
| 60 | 436 | 63 |
| 120 | 360 | 66 |
| 180 | 350 | 50 |

TABLE 1-continued

Vitamin B12 serum concentration in 6 volunteers after nasal administration of hydroxocobalamin in an isotonic aqueous solution.
dose: 500 µg hydroxocobalamin HCl
volume: 100 µl
concentration: 500 µg/100 µl = 50 µg/100 mg = 0.5%

| Time after administration (minutes) | Vit B12 pMol/l | Standard deviation (n = 6) |
|---|---|---|
| 240 | 345 | 51 |

The experiment as described in table 1, was repeated with nasal administration of 500 µg cyanocobalamin. The formulations were also tested as aerosol and with formulations containing thickening agents like methylcellulose 400 mPas 1-2% and hydroxypropylmethylcellulose 4000 mPas 1%. None of the formulations gave a result which was significantly different from the results as listed in table 1.

From these experiments we have drawn the conclusion, that the absorption of hydroxocobalamin and cyanocobalamin in the human nose takes place between 0–60 minutes after nasal administration and the maximum serum level (Cmax) is reached between 30–60 minutes (Tmax); and that—the nasal administration of the formulations as aerosol, as described in PCT/US86/00665, or the formulation containing thickening agents, as described in PCT/US 86/00793, does not, or insignificantly, influence or modify the rate and extent of the nasal absorption of Vitamin B12.

Continued investigations were carried out into the real mechanism of the nasal absorption of cyanocobalamin and hydroxocobalamin.

The following surprising results were obtained and the following conclusions were drawn:

the extent of nasal absorption of Vitamin B12, is mainly governed by the level of the concentration of Vitamin B12 in solubilized form, which is applied to the nasal mucosa.

the most effective concentrations of Vitamin B12 in the formulations for nasal administration are higher than 1%. The maximal concentration, that can be reached with cyanocobalamin is about 1%. Concentrations above 1% can only be obtained with hydroxocobalamin, because its good solubility in water. The solubility of hydroxocobalamin substances can be as high as 10%, which means that up to about 10 times more Vitamin B12 per unit of volume can be administered and subsequently absorbed nasally, when hydroxocobalamin is used.

This surprising finding is illustrated in table 2, showing the nasal absorption of hydroxocobalamin in 6 volunteers, after nasal administration of hydroxocobalamin in a concentration of 2%, which is a much higher concentration than maximally possible with cyanocobalamin. From the results it appears, that the absorption efficiency increases with the increasing concentration in the nasal formulation. In FIG. 1 the results from table 1 and table 2 are illustrated. The open circles represent the mean serum levels of hydroxocobalamin 0.5% (500 µg/100 µl) and the closed circles of hydroxocobalamin 2% (1500 µg/75 µl). The vertical bars represent the standard deviation.

The rise in Cmax after nasal administration of 2% hydroxocobalamin is several times higher than after administration of the 0.5% concentration. The concentration of hydroxocobalamin appears to be of decisive importance for an efficient nasal absorption. A superior nasal absorption of Vitamin B12 in therapy, can therefore, only be obtained by administration of a formulation containing a high concentration of hydroxocobalamin.

TABLE 2

Vitamin B12 serum concentration in 6 volunteers after nasal administration of hydroxocobalamin in an isotonic aqueous solution.
dose: 1500 µg hydroxocobalamin HCl
volume: 75 µl
concentration: 1500 µg/75 µl = 1500 µg/75 mg = 2%

| Time after administration (minutes) | Vit B12 pMol/l | Standard deviation (n = 6) |
|---|---|---|
| 0 | 203 | 18 |
| 10 | 504 | 71 |
| 20 | 731 | 109 |
| 30 | 830 | 124 |
| 40 | 839 | 116 |
| 60 | 802 | 110 |
| 120 | 712 | 75 |
| 180 | 688 | 59 |
| 240 | 746 | 67 |

According to the invention, the concentration of hydroxocobalamin in the nasal formulation is higher than 1%, preferably higher than 1.2%. The maximal solubility of hydroxocobalamin is about 10%, which is about 10× higher than can be reached with cyanocobalamin.

Nasal administration of the invented composition may take place according to any method, known from the pharmaceutical literature. It is also possible to use capsules, tampons or sponges, containing the hydroxocobalamin nasal composition.

According to the invention the nasal pharmaceutical composition contains hydroxocobalamin in a aqueous medium and the total composition possesses a low viscosity, less than 1000 cP, preferably below 100 cP.

The composition may also contain a number of excipients or additives, known from the pharmaceutical literature to be added to nasal formulations, such as preservatives, agents to adjust the pH or the osmolarity, surfactants, complexing agents, stabilizers and solubilizers.

Hydroxocobalamin in pharmaceutical formulations may be hydroxobalamin, hydroxocobalamin HCl, sulphate, acetate and similar derivatives. In water hydroxocobalamin occurs in equilibrium with aquocobalamin. In pharmaceutical compositions the quality of the hydroxocobalamin should comply with the requirements of a Pharmacopoeia. In the experiments, presented in table 1 and 2, hydroxocobalamin according to the requirements of the British Pharmacopoeia 1988 has been used.

I claim:

1. A method of treating Vitamin $B_{12}$ deficiency, said method comprising the intranasal administration of a pharmaceutical composition, said composition comprising one or more hydroxocobalamin compounds selected from the group consisting of hydroxocobalamin, hydroxocobalamin hydrochloride, hydroxocobalamin sulphate, hydroxcobalamin acetate, and any other pharmaceutically acceptable hydroxcobalamin salt, dissolved in an aqueous solution in a total concentration above 1% (w/w) and having a viscosity of less than 1000 cP.

2. The method of claim 1 wherein the total concentration of said one or more hydroxocobalamin compounds in said solution is in the range of 1.1–10% (w/w).

3. The method of claim 1 wherein said composition further comprises one or more additives selected from a preservative, an agent to adjust the pH, an agent to adjust the osmolarity, a surfactant, a completing agent, a stabilizing agent, and a solubilizer.

4. The method according to claim 1 wherein said composition is administered through a capsule, a unit dose vial, a nasal tampon, or a nasal sponge.

* * * * *